United States Patent
Panchanadikar

(10) Patent No.: US 9,808,265 B2
(45) Date of Patent: Nov. 7, 2017

(54) SYSTEM FOR ACCURATE GUIDE WIRE POSITIONING

(71) Applicant: Vijay Madhav Panchanadikar, Pune (IN)

(72) Inventor: Vijay Madhav Panchanadikar, Pune (IN)

( * ) Notice: Subject to any disclaimer, the term of this patent is extended or adjusted under 35 U.S.C. 154(b) by 450 days.

(21) Appl. No.: 14/362,133

(22) PCT Filed: Dec. 19, 2012

(86) PCT No.: PCT/IN2012/000829
§ 371 (c)(1),
(2) Date: Jun. 2, 2014

(87) PCT Pub. No.: WO2013/098853
PCT Pub. Date: Jul. 4, 2013

(65) Prior Publication Data
US 2014/0336671 A1    Nov. 13, 2014

(30) Foreign Application Priority Data

Dec. 20, 2011    (IN) .......................... 3571/MUM/2011

(51) Int. Cl.
*A61B 17/17*    (2006.01)
*A61B 17/88*    (2006.01)
*A61B 90/11*    (2016.01)
*A61B 17/90*    (2006.01)

(52) U.S. Cl.
CPC ...... *A61B 17/1703* (2013.01); *A61B 17/8897* (2013.01); *A61B 90/11* (2016.02); *A61B 2017/90* (2013.01)

(58) Field of Classification Search
CPC ........................... A61B 17/1703; A61B 90/11
See application file for complete search history.

(56) References Cited

U.S. PATENT DOCUMENTS

2009/0254098 A1* 10/2009 Christian ............... A61B 34/10
                                                               606/130
2010/0030219 A1*  2/2010 Lerner ............... A61B 17/1703
                                                               606/87

* cited by examiner

*Primary Examiner* — Andrew Yang

(57) ABSTRACT

The present invention provides system for accurate guide wire positioning. The said system comprises Jigs with series of holes at different angle. Guide wire can be positioned at different version with or without change in angle depending on the position of guide wire. Also, jig provides flexibility of change in version with or without change of entry point of insertion of guide wire in bone. Also, system comprises external drive which superimposes grid guide of parallel lines or line extensions on the image of guide wire. This drive also projects the future position of the said wire guide. From the projection, if correction is required in the guide wire positioning then it can be changed with the help of said jig.

6 Claims, 8 Drawing Sheets

SYSTEM FOR ACCURATE GUIDE WIRE POSITIONING

This application is Continued Prosecution Application (CPA) corresponding original application Ser. No. 14/362,133 entitled "System for accurate guide wire positioning."

FIELD OF INVENTION

The present invention relates to a system for accurate guide wire positioning in orthopedic surgery.

BACKGROUND OF INVENTION

In many orthopedic surgeries, accurate guide wire placement is needed before implant is positioned. Guide wire positioning is normally done by trial and error method under C-arm image guidance. In this method, using C-arm image of guide wire in bone is taken in one plane then; C-arm is rotated in 90° and image in second plane, perpendicular to first plane is taken. If the wire is not in correct position, then again wire is inserted and position of said wire is checked in both planes using same method. This method takes more time and does not give assurance of correct guide wire positioning.

It is always challenging to perform this guide wire positioning in minimum time with maximum accuracy.

A solution is needed wherein the guide wire can be passed in accurate position in least possible time without resorting to the above trial and error method.

OBJECTS OF THE INVENTION

The main object of the present invention is to provide system for accurate positioning of guide wire in least possible time.

SUMMARY OF THE INVENTION

The present invention describes a system comprising of jigs and external drive which is able to guide and project respectively the direction of the guide wire or K wire into the bone or body part from a position outside, without actually going into the bone or body part.

The said jig comprises holes at particular angles on front and rear sides. Guide wire or K wire is guided through said holes with help of sleeves. This jig provides flexibility of changing version with or without change in angle. Also, jig allows change in version with or without controlled change of entry point of insertion of guide wire in bone.

Also, said external drive superimposes grid guide of parallel lines on Guide wire image. The said system superimposes grid guide of line extension on guide wire image. After adjusting the positioning of grid wire in one plane same steps are repeated in plane perpendicular to first plane. In other embodiment of the present invention, said external drive creates 3 dimensional image of bones from 2 dimensional images obtained from Xray/C arm and projects future position of guide wire by line extension into 3D image of bones.

After fixing the position of guide wire in both planes, guide wire is inserted in the bone.

Figure 1:
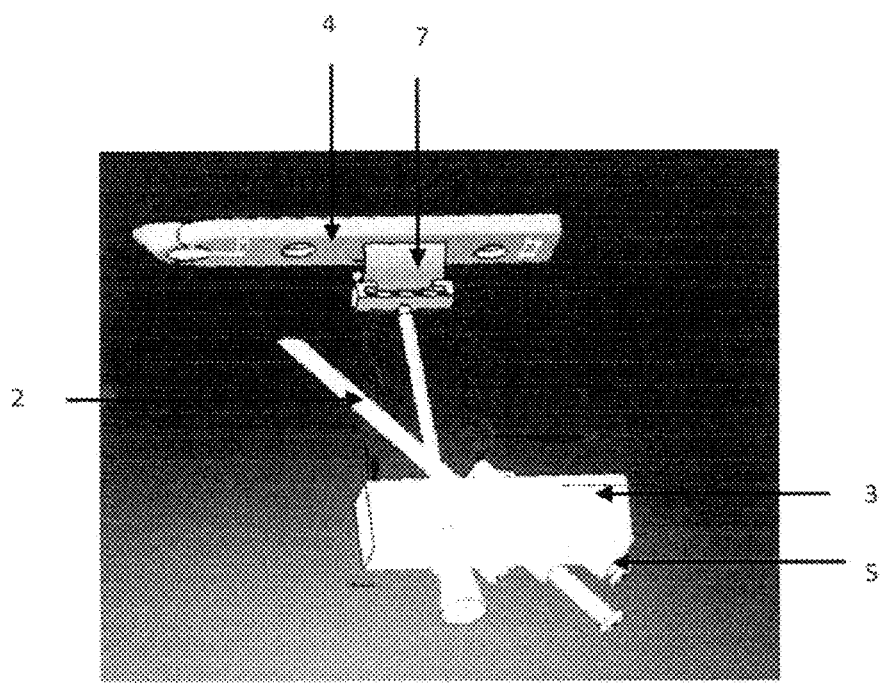
FIG. 1 describes construction of jig used for guide wire positioning

Following Table No. 1 describes the legends used in the drawings and their description

TABLE NO. 1

| Legends | Legend Description |
|---------|--------------------|
| 1 | Guide wire |
| 2 | Sleeve |
| 3 | Front plate |
| 4 | Rear plate |
| 5 | Holes on front plate |
| 6 | Threaded Screw |
| 7 | Rotatable hinge |
| 8 | C shaped plate |
| 9, 10 | Threaded or non threaded holes |
| 11 | Threaded hollow sleeve |
| 12 | Bolt |
| 13 | Nuts |
| 14 | Eccentric threaded hollow sleeve |
| 15 | Measuring scale |
| 16 | Lower plate |
| 17 | Upper plate |
| 18 | Hinge ball socket |
| 19 | Grid guide of parallel lines |

DETAILED DESCRIPTION OF THE DRAWINGS

The present invention is illustrated by way of example, and not by way of limitation, in the figures of the accompanying drawings and in which like reference numerals refer to similar elements.

The present invention is better understood by reference to the detailed figures and description set forth herein.

FIG. 1 describes the construction of jig. Jig comprises front plate (3) and rear plate (4). Front plate has series of holes (5) at particular angles and rear plate has slot to insert the guide wire and screws to stabilize it on bone. The said holes (5) are made at particular angle ranging from 80° to 130°. Depending on the type of surgery, angle of guide wire positioning is decided. Sleeve (2) passed through holes helps in positioning the guide wire (1). Front plate (3) and rear plate (4) of the jig are joined together with the help of rotatable hinge (7) and screw (6) which allow controlled change of version. Curvature of said rotatable hinge (7) ensures the entry point of sleeve (2) does not change.

The guide wire (1) is positioned by inserting it through particular holes (5). After taking the image of guide wire and getting the projection of the said guide wire (1), if the position of the guide wire is not correct, then the guide wire (1) is repositioned in said holes (5) of jig having different angle.

Change in the guide wire positioning with respect to version, angle or entry point of insertion is made based on the projected image of guide wire.

After projecting this position in anterio-posterior (AP) plane, image or X-ray of guide wire in lateral plane which is perpendicular to first plane is captured.

Figure 2:
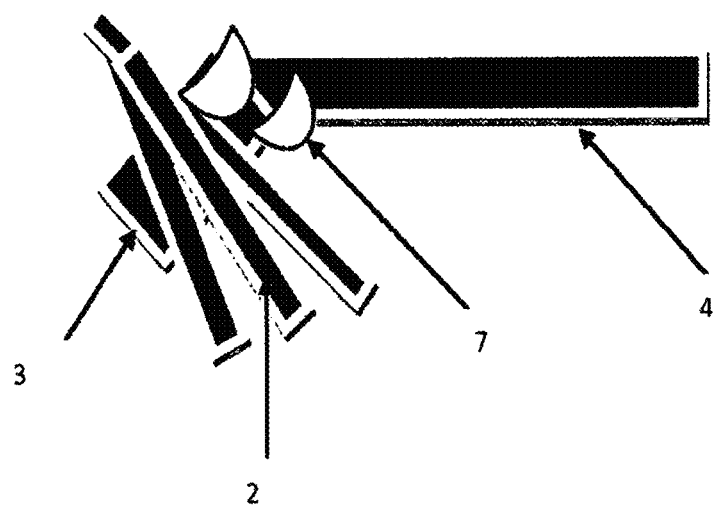
FIG. 2 shows another embodiment of jig shown in FIG. 1
Figure 3:
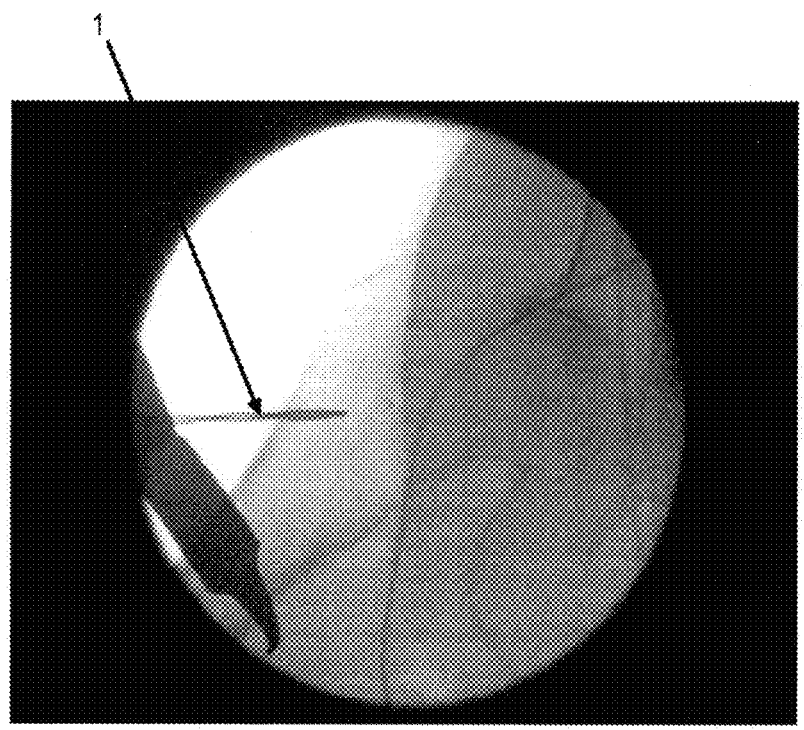
FIG. 3 shows the image of guide wire in anterio-posterior (AP) plane
Figure 4:
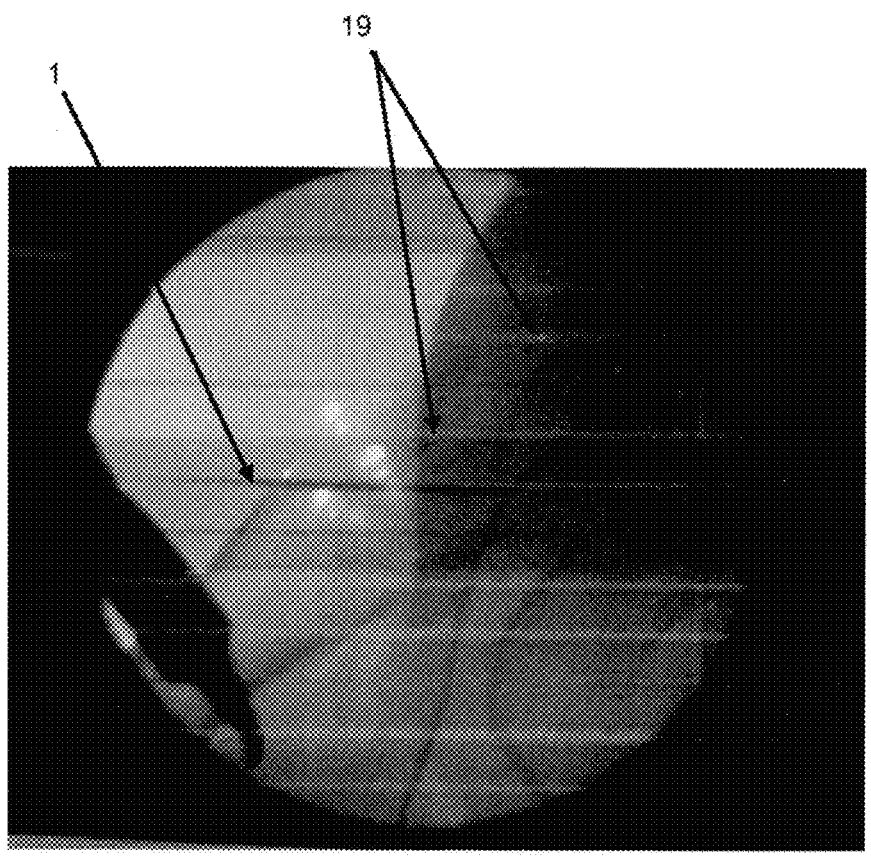
FIG. 4 shows the image of superimposed parallel lines of grid guide in anterio-posterior (AP) plane
Figure 5:
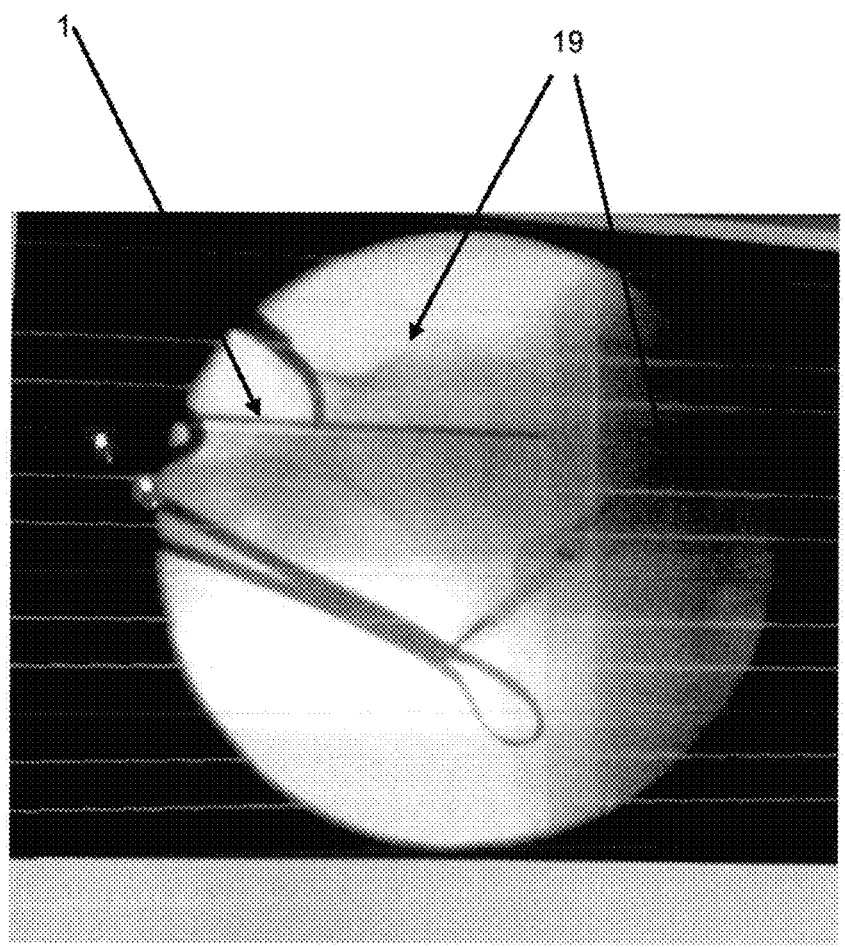
FIG. 5 shows the image of superimposed parallel lines of grid guide in lateral plane (LP).

FIG. 2 describes one embodiment of jig, comprises a rear plate (4) obliquely attached to front plate (3), both plates joined together with rotatable hinge (7) and screw (6), sleeves (2) passing through holes (5) in front plate (3) at an angles ranging between 100 to 140 Degrees, all the sleeves (2) attached at different angles and versions and the said sleeves converge on single entry point.

Guide wire (1) is positioned in the sleeve (2) and image is captured by conventional means, with the help of external drive, future position of the guide wire is projected by line extension and if the guide wire (1) is not positioned correctly then guide wire (1) or sleeve (2) is inserted in another hole of different angle. Now image is captured in another plane and with help of rotatable hinge (7), rear plate (4) is rotated to change the version without changing the entry point to get accurate guide wire positioning.

Figure 6:
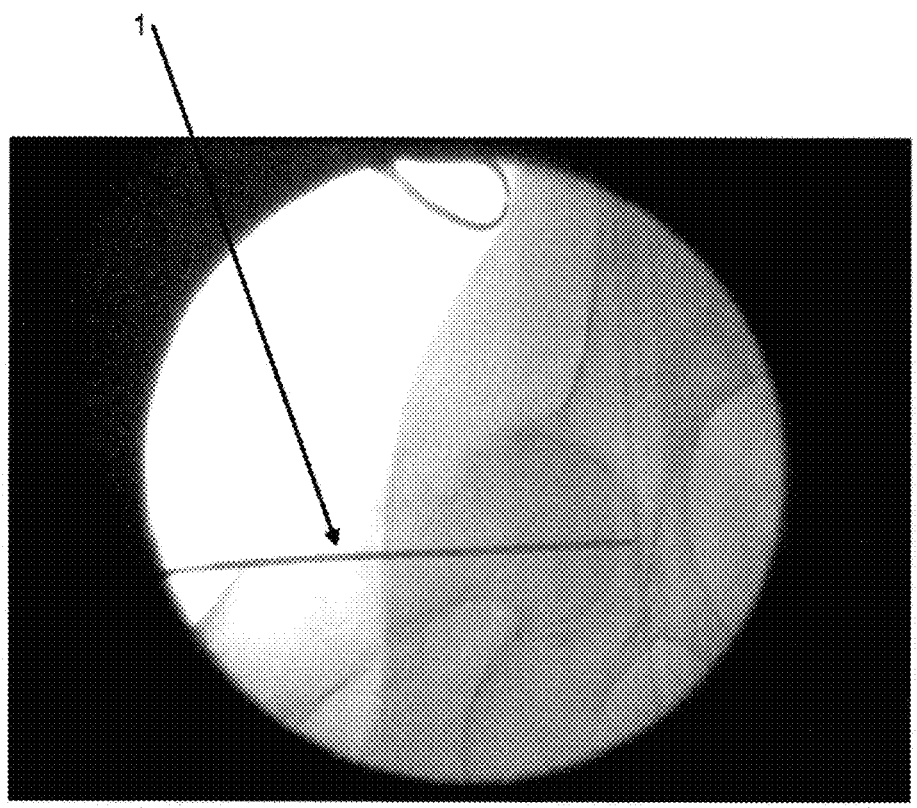
FIG. 6 shows the image of actual guide wire driven into the bone

FIG. 6 shows the image of guide wire in anterio-posterior (AP) plane.

At the time of orthopedic surgery, guide wire (1) which is not driven into the bone, is positioned and image of that position is taken by conventional means.

Figure 7:
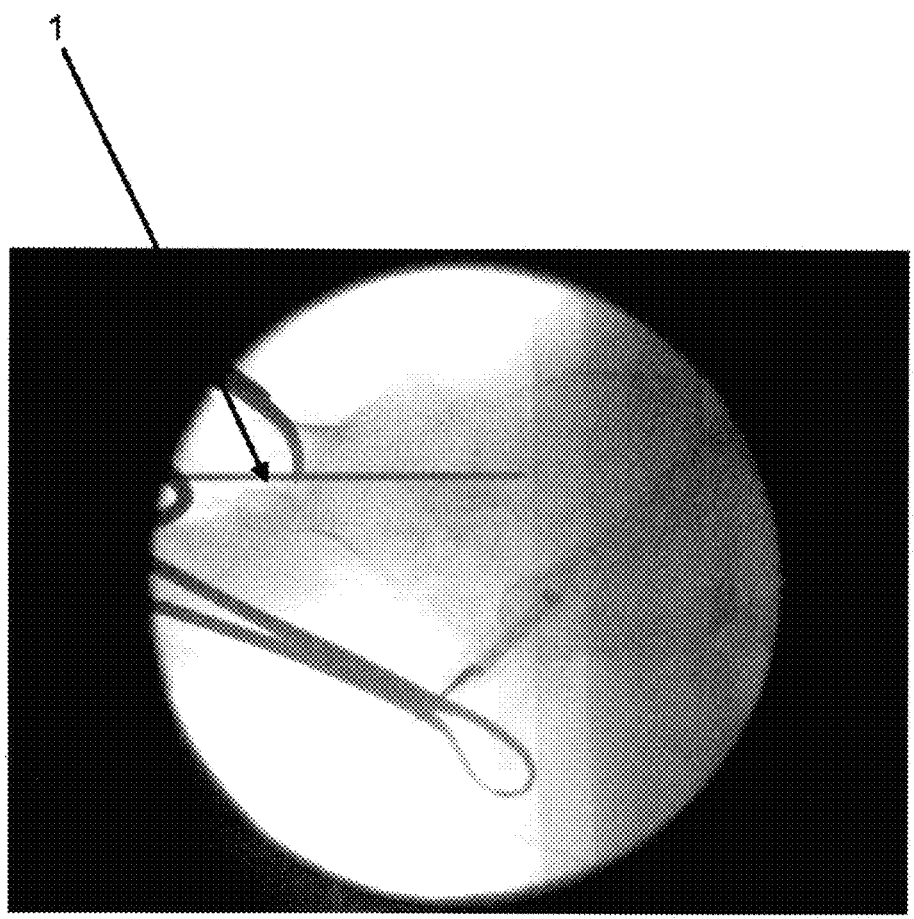
FIG. 7 shows the image of guide wire in lateral plane (LP)

FIG. 7 shows the image of superimposed parallel lines of grid guide in anterio-posterior (AP) plane.

With the help of external drive system, grid guide of parallel lines (19) is superimposed on said guide wire image (FIG. 6). This projects future position of the guide wire (1). Adjustments in positioning of guide wire are done using grid as guide with the help of jig.

Figure 8:
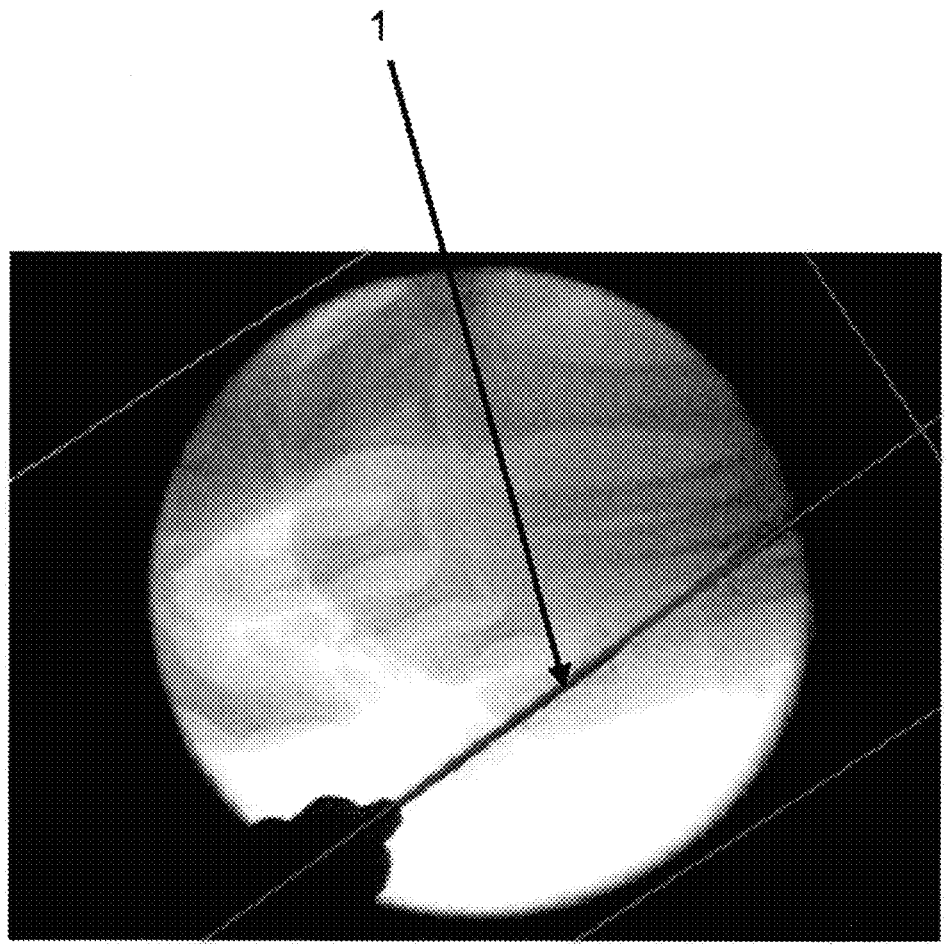
FIG. 8 shows projection of future position of guide wire by external drive

FIG. 8 shows the image of superimposed parallel lines of grid guide (19) in lateral (LP) plane.

Again with the help of external drive, the grid guide of parallel lines (19) is superimposed on the guide wire image taken in the lateral plane. This projects future position of the guide wire (1). If the lateral plane positioning of the guide wire is not correct, then guide wire is again repositioned by keeping the position of said guide wire in the anterio-posterior (AP) plane constant.

As the position of guide wire in the anterio-posterior (AP) plane is fixed by jig and system, only version position of guide wire in the lateral (LP) plane will be changed eliminating trial and error method.

FIG. 9 shows, the image of actual guide wire driven into the bone, after deciding the final position of guide wire in both the planes.

FIG. 10 shows the image of guide wire in lateral plane (LP). At the time of orthopedic surgery, guide wire (1) which is not driven into the bone, is positioned and image of that position is taken by conventional means.

FIG. 11 describes one embodiment of the invention.

The said external drive projects the future position of guide wire (1) by line extension. By seeing the future position of guide wire, accurate adjustment in position of guide wire is possible.

I claim:

1. System for accurate guide wire positioning comprises,
    a) jig comprising front plate (3) and rear plate (4) wherein front plate (3) comprises at least two holes (5) at different angles for positioning guide wire (1) and rear plate (4) comprising at least one slot/hole, sleeve (2) attached to front plate (3) for controlling the position of guide wire (1) and a rotatable hinge (7) attaching front (3) and rear plate (4);
    b) External drive which projects the future position of guide wire by line extension into body part from a position outside.

2. The system for accurate guide wire positioning as claimed in claim 1, wherein the external drive superimposes grid guide of parallel lines (8) on the guide wire image to determine the future position of guide wire by line extension.

3. The system for accurate guide wire positioning as claimed in claim 1, wherein the external drive converts 2 dimensional image to 3 dimensional format and shows the future position of guide wire inside bone by line extension from the image of the said guide wire.

4. The system for accurate guide wire positioning as claimed in claim 1, wherein the Jig comprises of front plate (3) having at least two holes (5) at angle ranging between 80° to 130°.

5. The system for accurate guide wire positioning as claimed in claim 1, wherein the Jig comprises, a front plate (3) and a rear plate (4) attached together by rotatable hinge (7), a sleeve (2) attached to front plate (3) at angles wherein, said angles converge at single point and the guide wire (1) is positioned through said sleeve (2), and by rotating the said rotatable hinge (7), version is changed without change in entry point.

6. Process for guide wire positioning by using system as claimed in claim 1 comprising
    a) positioning of the guide wire on the surface of bone by inserting guide wire (1) in the hole of a jig,
    b) capturing the image in one plane by conventional means,
    c) getting the superimposed grid guide of parallel lines (8) by line extension on guide wire image projecting future position of said guide wire by external drive,
    d) repositioning the guide wire (1) in the said hole (5) of the jig using projected grid of parallel lines by line extension, if the position of the guide wire is not correct wherein, either the version and/or the angle of guide wire is changed or kept constant according to the requirement,
    e) capturing the image of guide wire in lateral plane (LP) perpendicular to anterio-posterior (AP) plane,
    f) Conversion of obtained 2 dimensional image to 3 dimensional format,
    g) getting the superimposed grid guide of parallel lines (8) by line extension on guide wire image projecting future position of said guide wire by external drive,
    h) repositioning the guide wire in the said hole of the jig without disturbing the position in anterio-posterior plane, using projected grid of parallel lines if the position of the guide wire is not correct wherein, either the version and/or the angle of guide wire is changed or kept constant according to the requirement,
    i) inserting the guide wire (1) in the body part.

* * * * *